United States Patent [19]

Müller et al.

[11] Patent Number: 4,680,365

[45] Date of Patent: Jul. 14, 1987

[54] METHOD FOR PREPARING ACETOXYSILOXANES AND ORGANO(POLY)SILOXANES HAVING HALOGEN BONDED TO SILICON

[75] Inventors: Johann Müller; Christa Trieschmann; Walter Doskocil; Gerhard Preiner, all of Burghausen, Fed. Rep. of Germany

[73] Assignee: Wacker-Chemie GmbH, Munich, Fed. Rep. of Germany

[21] Appl. No.: 859,296

[22] Filed: May 5, 1986

[30] Foreign Application Priority Data

May 23, 1985 [DE] Fed. Rep. of Germany ....... 3518605

[51] Int. Cl.$^4$ ...................... C08G 77/06; C08G 77/08; C07F 7/04; C08F 283/12
[52] U.S. Cl. ........................................ 528/15; 528/12; 528/31; 528/25; 525/479; 556/442; 556/477

[58] Field of Search .................... 528/31, 25, 15, 479; 556/442, 477

[56] References Cited

U.S. PATENT DOCUMENTS 4,160,775  7/1979  Schilling, Jr. ...................... 556/440

*Primary Examiner*—Lewis T. Jacobs
*Assistant Examiner*—David W. Woodward

[57] ABSTRACT

Organo(poly)siloxanes having halogen bonded directly to silicon, or acetoxysiloxanes are prepared by reacting organo(poly)siloxanes having hydrogen bonded directly to silicon, with an allyl compound in the presence of metallic palladium, ruthenium or rhodium, or an acetylacetone or phosphine complex, or compound containing palladium, ruthenium or rhodium in which the allyl compound is an allyl halide having 3 carbon atoms per molecule or allyl acetate.

14 Claims, No Drawings

METHOD FOR PREPARING ACETOXYSILOXANES AND ORGANO(POLY)SILOXANES HAVING HALOGEN BONDED TO SILICON

The present invention relates to acetoxysiloxanes and organo(poly)siloxanes having halogen bonded directly to silicon and more particularly to a method for preparing acetoxysiloxanes and organo(poly)siloxanes having a halogen atom bonded directly to silicon.

BACKGROUND OF THE INVENTION

Heretofore, tris-(trimethylsiloxy)-acetoxysilane has been prepared in accordance with the procedure described in Canadian Patent No. 1,157,876 to N. N. Novicky.

Also, organo(poly)siloxanes having halogen bonded directly to silicon, specifically chlorine, have been prepared, heretofore, by reacting an organo(poly)siloxane having hydrogen that is bonded directly to silicon, with beta-methally chloride in the presence of metallic palladium or ruthenium ((Th. A. Barry et al, *Journal of Organic Chemistry*, Vol. 38, pp. 838–841).

It is, therefore, an object of the present invention to provide a method for preparing organo(poly)siloxanes having halogen that is bonded directly to silicon. Another object of the present invention is to provide a method for preparing organo(poly)siloxanes having halogen bonded directly to silicon by reacting an organo(poly)siloxane having hydrogen bonded directly to silicon with an allyl compound in the presence of metallic palladium, rhodium or ruthenium in high yields. Another object of the present invention is to provide a method for preparing organo(poly)siloxanes having halogen bonded directly to silicon in the presence of a minimal amount of catalyst. A further object of the present invention is to provide a method for preparing acetoxysiloxanes which does not result in the formation of corrosive by-products.

SUMMARY OF THE INVENTION

The foregoing objects and others which will become apparent from the following description are accomplished in accordance with this invention, generally speaking, by providing a method for preparing acetoxysiloxanes or organo(poly)siloxanes having halogen bonded directly to silicon which comprises reacting an organo(poly)siloxane having a hydrogen atom bonded directly to silicon with an allyl compound in the presence of a catalyst selected from the group consisting of metallic palladium, ruthenium, rhodium, or an acetylacetone or phosphine complex or composition containing palladium, ruthenium or rhodium, in which the allyl compound is an allyl halide having 3 carbon atoms per molecule or an allyl acetate.

DESCRIPTION OF THE INVENTION

In the method for preparing acetoxysiloxanes or organo(poly)siloxanes having a halogen bonded directly to silicon, an organo(poly)siloxane having hydrogen bonded directly to silicon is reacted with an allyl compound in the presence of a catalyst selected from metallic palladium, ruthenium or rhodium, or an acetylacetone or phosphine complex or composition containing palladium, ruthenium or rhodium, in which the allyl compound is an allyl halide having 3 carbon atoms per molecule, or an allyl acetate.

Heretofore, is was not known that hydrogen bonded directly to silicon was influenced by silicon substituents other than siloxane oxygen atoms. Therefore, it is possible to use in the method of this invention, any organo(poly)siloxanes in which hydrogen is bonded directly to silicon. However, preferred organo(poly)siloxanes having hydrogen bonded to silicon are those of the following formulas:

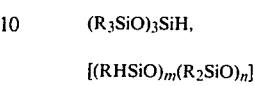

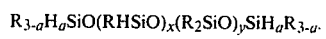

and $$R_{3-a}H_aSiO(RHSiO)_x(R_2SiO)_ySiH_aR_{3-a}.$$

In these formulas, R is the same or different and represent monovalent hydrocarbon radicals, halogenated monovalent hydrocarbon radicals or monovalent aliphatic radicals containing carbon, hydrogen, ether-oxygen and fluorine atoms and all of the R radicals are free of aliphatic carbon-carbon multiple bonds, or trialkylsiloxy radicals, especially trimethylsiloxy radicals. The value of a is 0 or 1 and may be different in the same molecule; m is an integer having a value of 3 to 8; n is an integer having a value of 0 to 7; where the sum of the values of m+n is no more than 8; and where x is 0 or an integer having a value of at least 1, with the proviso that at least one a or x is an integer other than 0; and y is 0 or an integer having a value of at least 1.

It is preferred that the sum of the values x+y be kept low in order to ensure that the viscosity of the linear organo(poly)siloxanes of the above formula does not exceed 50,000 mPa.s at 25° C. Examples of such carbon radicals represented by R are alkyl radicals, such as the methyl, ethyl, propyl, isopropyl, butyl and sec-butyl radical, as well as octadecyl radicals; cycloalkyl radicals, such as the cyclohexyl radical and methylcyclohexyl radicals; aryl radicals such as the phenyl radical and diphenyl radical; alkaryl radicals such as the tolyl radicals; and aralkyl radicals, such as the benzyl radical.

Examples of halogenated hydrocarbon radicals represented by R are the 3,3,3-trifluoropropyl radicals and o-, p- and m-chlorophenyl radicals, as well as the beta-chloroethyl radical.

Examples of monovalent aliphatic radicals represented by R consisting of carbon, hydrogen, ether-oxygen and fluorine atoms, are the 1,1,2,2,3,3-hexafluoropropyloxypropyl radical and the 1,1,2,2-tetrafluoroethoxypropyl radical. Because of their availability, it is preferred that at least 80 percent of the number of organic radicals in the organo(poly)siloxanes used in the method of this invention, i.e., the R radicals in the above formulas, be methyl radicals.

Specific examples of organo(poly)siloxanes having hydrogen bonded to silicon, which may be used in the method of this invention, are tris-(trimethylsiloxy)-silane, which due to its content in siloxane-oxygen atoms really is an organosiloxane, notwithstanding the fact that it is referred to as a "silane" and 1,1,1,3,3-pentamethyldisiloxane, 1,1,3,3-tetramethyldisiloxane, dimethylpolysiloxanes having dimethylhydrogensiloxy terminal units, cyclic organopolysiloxanes containing 3 methylhydrogensiloxane units and a cyclic organopolysiloxane having a methylhydrogen siloxane unit and 3 dimethylsiloxane units, as well as methylhydrogenpolysiloxanes that are end-blocked by trimethylsiloxy groups and copolymers of methylhydrogenpolysiloxane and dimethylsiloxane units which are end-blocked by trimethylsiloxy groups.

When metallic palladium, ruthenium or rhodium or mixtures of these elements are used as catalysts, it is preferred that the metal be finely dispersed, as is generally the case, when such catalysts are used. The metallic palladium, ruthenium or rhodium can be present on carriers which are inert with respect to such metals and the other components of the reaction. Examples of such inert carriers are activated charcoal, silicon dioxide and aluminum oxide.

Specific examples of acetylacetone or phosphine complexes and especially triphenylphosphine complexes or acetylacetone or phosphine complexes of palladium, ruthenium or rhodium are palladium-bisacetylacetonate; chlorotris-(triphenylphosphine)-rhodium; the complex of the formula $Rh(acac)(P(C_6H_5)_3)_2$; rhodium-bis-acetylacetonate, ruthenium-tris-acetylacetonate; the complex of formula $Ru(acac)_2(P(C_6H_5)_3)_2$ and the complex of formula $RuCl_2(P(C_6H_5)_3)_2$, wherein "acac" represents "acetylacetonate".

When an allylhalide is used, it is preferred that metallic palladium and activated charcoal, palladium-bis-acetylacetonate, ruthenium-tris-acetylacetonate and the complex of the formula $((C_6H_5)_3P)_3RhCl$ be used. Palladium supported on activated charcoal is particularly preferred when an allylhalide is used.

When allyl acetate is used, it is preferred that metallic palladium on activated charcoal, metallic ruthenium on activated charcoal and the aforementioned acetylacetonates and ruthenium complex be employed. When allyl acetate is used, metallic palladium on activated charcoal and metallic ruthenium on activated charcoal are especially preferred.

Mixtures containing at least one of the elements palladium, ruthenium and rhodium and at least one complex and at least one acetylacetone or phosphine composition, especially triphenylphosphine and one of the aforementioned elements, may be used.

It is preferred that the metallic palladium, ruthenium or rhodium as well as the acetylacetone or phosphine complex, or the acetylacetone or phosphine compositions of the aforementioned precious metals be used in an amount from 50 to 1000 ppm by weight (parts per million), based on the elemental metal and the combined weights of the organo(poly)siloxane that contains hydrogen which is bonded directly to silicon, and the allylhalide or allyl acetate.

The halide in the allylhalide or the 3-halogenpropene(1) may be chlorine, bromine or iodine. Chlorine is preferred because it is more readily available.

Preference is given to allylhalide or allyl acetate containing from 0.5 to 5 mols per gram/atom of hydrogen that is bonded directly to silicon.

The method of this invention is preferably carried out at temperatures between about 25° and 200° C. and at atmospheric pressure since that is the most economical method, i.e., at 1020 hPa, or approximately 1020 hPa. Since the propylene which is also produced by the method of this invention is gaseous even at room temperature, using lower pressures may be advantageous.

In the method of this invention, the reaction components and the catalyst may be mixed together and then increased to the desired temperature. When the organo(poly)siloxane having hydrogen bonded directly to silicon is particularly reactive, for example, pentamethyldisiloxane, it can be added dropwise to a mixture containing the catalyst and the allylhalide or allyl acetate, or such a mixture can be added dropwise to the siloxane.

When relatively highly viscous organo(poly)siloxanes are used, the method of this invention can be conducted in the presence of an inert solvent that is inert to the components of the reaction catalyst, for example, toluene, tetrahydrofuran or dioxane or a mixture comprising at least two such solvents.

The solvent and any unreacted allylhalide or unreacted allyl acetate may be separated by evaporation, optionally under decreased pressure, from the organo(poly)siloxane comprising halogen that is bonded directly to silicon or the acyloxysiloxane obtained in accordance with the method of this invention.

If desired, the catalyst can be removed, for example, by filtration from the organo(poly)siloxane comprising halogen that is bonded directly to silicon or the acyloxysiloxane prepared in accordance with the method of this invention.

The organo(poly)siloxanes having halogen which is bonded directly to silicon, or the acyloxysiloxanes of this invention, may be used for the same purposes for which the heretofore-known organo(poly)siloxanes comprising halogen that is bonded directly to silicon or acyloxysilanes, have been or could have been used heretofore. For example, these organo(poly)siloxanes or acyloxysiloxanes may be used to prepare organo(poly)siloxanes having organofunctional groups and, when their chains are short, as in the case of pentamethylchlorodisiloxane, they may be used for the introduction of protective groups in organic chemistry. Additionally, the acyloxysiloxanes prepared in accordance with this invention may, for example, be used to prepare graft polymers by reacting them with organic polymers containing alcoholic hydroxyl groups, such as a polyester containing alcoholic hydroxyl groups.

EXAMPLE 1

About 306 g of allylchloride are added dropwise with constant stirring to a mixture containing 592 g of 1,1,1,3,3-pentamethyldisiloxane and 200 ppm by weight of palladium (based on the total weight of the disiloxane and the allylchloride) in the form of palladium on activated charcoal (5 percent by weight of palladium and 95 percent by weight of activated charcoal) heated to 50° C. The temperature of the mixture increases to 96° C. during the addition. After all of the allylchloride has been added, stirring is continued for an additional 30 minutes. $^1$H-NMR analysis shows that the reaction mixture contains approximately 95 mol percent of 1,1,1,3,3-pentamethyl-3-chlorosiloxane (based on the siloxane portion). The desired chlorosiloxane is obtained by fractional distillation from the mixture with a purity of 99 percent by weight.

EXAMPLE 2

A mixture containing 38.4 g of allylchloride, 33.5 g of 1,1,3,3-tetramethyldisiloxane and 200 ppm by weight of palladium (based on the total weight of the disiloxane and the allylchloride) in the form of palladium bis-acetylacetonate is heated slowly with constant stirring. When the temperature of the mixture reaches 40° C., a violent reaction takes place in which the temperature rises to 100° C. After the reaction has subsided, stirring is continued for an additional 15 minutes. $^1$H-NMR analysis shows that the reaction mixture contains 84 mol percent of 1,1,3,3-tetramethyl-1,3-dichlorodisiloxane (based on the siloxane portion).

EXAMPLE 3

The method described in Example 2 is repeated, except that the 200 ppm by weight of palladium are substituted with 200 ppm by weight (based on the weight of the disiloxane and the allylchloride) of rhodium in the form of a complex having the formula $[(C_6H_5)_3P]_3RhCl$. After the reaction has subsided, stirring is continued for an additional 15 minutes. $^1$H-NMR analysis of the resultant mixture shows that 60 mol percent of 1,1,3,3-tetramethyl-2,3-dichlorodisiloxane is present in the mixture (based on the siloxane portion).

EXAMPLE 4

The method described in Example 2 is repeated, except that the 200 ppm by weight of palladium are substituted with 200 ppm by weight (based on the total weight of the disiloxane and the allylchloride) of ruthenium in the form of ruthenium-trisacetylacetonate. After the reaction had subsided and after stirring had been continued for an additional 15 minutes, $^1$H-NMR analysis of the resultant mixture indicated that 40 mol percent of 1,1,3,3-tetramethyl-1,3-dichlorodisiloxane is present, and after stirring for 80 minutes, 70 mol percent of 1,1,3,3-tetramethyl-1,3-dichlorodisiloxane is present (based on the siloxane portion).

EXAMPLE 5

A mixture containing 12.1 g of allylbromide, 14.8 g of 1,1,1,3,3-pentamethyldisiloxane and 200 ppm by weight (based on the total weight of the disiloxane and the allylbromide) of palladium in the form of palladium on activated charcoal (5 percent by weight of palladium and 95 percent by weight of activated charcoal) are slowly heated to 70° C. under constant stirring. After stirring for 2 hours at 70° C. $^1$H-NMR analysis shows that the reaction mixture contains 77 mol percent, based on the siloxane portion, of 1,1,1,3,3-pentamethyl-3-bromodisiloxane.

EXAMPLE 6

A mixture containing 38.3 g of allyliodide, 14.8 g of 1,1,1,3,3-pentamethyldisiloxane and 200 ppm by weight (based on the total weight of the disiloxane and the allylhalide) of palladium in the form of palladium supported activated charcoal (5 percent by weight of palladium and 95 percent by weight of activated charcoal) is heated to 80° C. with constant stirring. After stirring for about 2 hours at 80° C., $^1$H-NMR analysis shows that the mixture contains 52 mol percent of 1,1,1,3,3-pentamethyl-3-iododisiloxane based on the siloxane portion.

EXAMPLE 7

To a mixture that has been heated to 40° C. and which consists of 38.3 g of allylchloride and 200 ppm by weight (based on the total weight of the organopolysiloxane and the allylhalide) of palladium in the form of palladium supported activated charcoal (5 percent by weight of palladium and 95 percent by weight of activated charcoal) are added dropwise and with stirring to 13.4 g of a trimethylsiloxy endblocked copolymer consisting of 50 mol percent of methylhydrogensiloxane units and 50 mol percent dimethylsiloxane units having a viscosity of 250 mPa.s at 25° C. After stirring for 3 days at 40° C., 90 mol percent of the hydrogen that is bonded directly to silicon has been substituted by chlorine which is bonded directly to silicon.

EXAMPLE 8

A mixture containing 13.4 g of tris-(trimethylsiloxy)-silane, 3.8 g of allylchloride and 200 ppm by weight (based on the total weight of the organosilicon compound and the allylchloride) of palladium in the form of palladium supported on activated charcoal (5 percent by weight of palladium and 95 percent by weight of activated charcoal) is heated to boiling under reflux (approx. 80° C.). After refluxing for 5 hours, $^1$H-NMR analysis shows that the reaction mixture contains 30 mol percent of tris-(trimethylsiloxy)chlorosilane, and after refluxing for 9 hours the reaction mixture contains 90 mol percent of tris-(trimethylsiloxy)-chlorosilane.

EXAMPLE 9

A mixture containing 14.8 g of 1,1,1,3,3-pentamethyldisiloxane, 10.0 g of allyl acetate (acetic acid allylester) and 0.01 g of palladium supported on activated charcoal, in which the 0.1 g refers to the total weight of the charcoal and the palladium, is heated to boiling under reflux (approximately 105° C.) for 4 hours. The 1,1,1,3,3-pentamethyl-3-acetoxydisiloxane yield is quantitative.

EXAMPLE 10

A mixture containing 296 g of tris-(trimethylsiloxy)silane, 110 g of allyl acetate and 2.4 g of ruthenium supported on activated charcoal (5 percent by weight of ruthenium and 95 percent by weight of activated charcoal), in which the 2.4 g refers to the total wieght of the charcoal and the ruthenium, are heated to boiling under reflux (approx. 105° C.) for 4 hours. The tris-(trimethylsiloxy)-acetoxysilane yield is quantitative.

EXAMPLE 11

A mixture containing 51.2 g of allyl acetate, 33.5 g of 1,1,3,3-tetramethyldisiloxane and 200 ppm by weight (based on the total weight of the disiloxane and the allyl acetate) of palladium in the form of palladium-bis-acetylacetonate, is slowly heated with constant stirring. At 50° C., a violent reaction takes place and the temperature rises to about 105° C. After the reaction has somewhat subsided, stirring is continued for an additional 15 minutes. $^1$H-NMR analysis shows that the reaction mixture contains 80 mol percent (based on the siloxane portion) of 1,1,3,3-tetramethyl-1,3-diacetoxydisiloxane.

EXAMPLE 12

The procedure of Example 11 is repeated, except that 200 ppm (based on the total weight of the disiloxane and the allyl acetate) of rhodium in the form of a complex having the formula $[(C_6H_5)_3P]_3RhCl$ are substituted for the 200 ppm by weight of palladium used in Example 11. After the reaction has subsided and after stirring for an additional 30 minutes, $^1$H-NMR analysis shows that the reaction mixture contains 70 mol percent of 1,1,3,3-tetramethyl-1,3-diacetoxydisiloxane, based on the siloxane portion.

EXAMPLE 13

The procedure of Example 11 is repeated, except that 200 ppm by weight (based on the total weight of disiloxane and allyl acetate) of ruthenium in the form of ruthenium trisacetylacetonate are substituted for the 200 ppm of palladium used in Example 11. After the reaction has somewhat subsided and after stirring for an additional 30 minutes, $^1$H-NMR analysis indicates that the reaction mixture contains 50 mol percent, and after stirring for an additional 120 minutes, 85 mol percent of 1,1,3,3-tetramethyl-1,3-diacetoxydisiloxane, based on the siloxane portion.

EXAMPLE 14

To a mixture heated to 40° C. and containing 51.2 g of allyl acetate and 200 ppm by weight (based on the total weight of the organopolysiloxane and the allyl acetate) of palladium in the form of palladium supported on activated charcoal (5 percent by weight of palladium and 95 percent by weight of activated charcoal), are added dropwise and with constant stirring, 13.4 g of a trimethylsiloxy endblocked copolymer which consists of 50 mol percent of methylhydrogensiloxane units and 50 mol percent of dimethylsiloxane units having a viscosity of 250 mPa.s at 25° C. After stirring for 3 days at 60° C., 90 mol percent of the hydrogen that is bonded directly to silicon has been substituted with acetoxy groups.

In none of the above Examples is an addition product of hydrogen on allylhalide or allyl acetate observed in the reaction mixture in addition to the organo(poly)siloxane having halogen bonded directly to silicon or acyloxysiloxane and unreacted organo(poly)siloxane having hydrogen bonded directly to silicon.

What is claimed is:

1. A method for preparing acetoxysiloxanes or organo(poly)siloxanes having halogen bonded directly to silicon, which comprises reacting an organopolysiloxane having hydrogen bonded directly to silicon, with an allyl compound in the presence of a catalyst selected from the group consisting of metallic palladium, ruthenium, rhodium, an acetylacetone complex of a metal selected from palladium, ruthenium or rhodium, a phosphine complex of a metal selected from palladium, ruthenium or rhodium, an acetylacetone composition containing a metal selected from the group consisting of palladium, ruthenium and rhodium and a phosphine composition containing palladium, ruthenium or rhodium, in which the allyl compound is selected from the group consisting of an allylhalide having 3 carbon atoms per molecule and an allyl acetate.

2. The method of claim 1, wherein the allylhalide is selected from the group consisting of an allylchloride, allylbromide or allyliodide.

3. The method of claim 2, wherein the allylhalide is allylbromide.

4. The method of claim 2, wherein the allylhalide is allyliodide.

5. The method of claim 1, wherein the organo(poly)siloxanes having halogen bonded directly to silicon are prepared by reacting an organo(poly)siloxane having hydrogen bonded directly to silicon with an allyl halide in the presence of a catalyst selected from the group consisting of metallic palladium, ruthenium and rhodium.

6. The method of claim 5, wherein the catalyst is metallic ruthenium.

7. The method of claim 5, wherein the catalyst is metallic rhodium.

8. The method of claim 1, wherein the organo(poly)siloxanes having halogen bonded directly to silicon are prepared by reacting an organo(poly)siloxane having hydrogen bonded directly to silicon with an allyl halide in the presence of a catalyst selected from the group consisting of an acetylacetone complex of a metal selected from the group consisting of palladium, ruthenium and rhodium and an acetylacetone composition containing a metal selected from the group consisting of palladium, ruthenium and rhodium.

9. The method of claim 1, wherein the organo(poly)siloxanes having halogen bonded directly to silicon are prepared by reacting an organo(poly)siloxane having hydrogen bonded directly to silicon with an allyl halide in the presence of a catalyst selected from the group consisting of a phosphine complex of a metal selected from the group consisting of palladium, ruthenium and rhodium and a phosphine composition containing a metal selected from the group consisting of palladium, ruthenium and rhodium.

10. The method of claim 1, wherein the acetoxysiloxanes are prepared by reacting an organo(poly)siloxane having hydrogen bonded directly to silicon with an allyl acetate in the presence of a catalyst selected from the group consisting of metallic palladium, ruthenium and rhodium.

11. The method of claim 1, wherein the acetoxysiloxanes are prepared by reacting an organo(poly)siloxane having hydrogen bonded directly to silicon with an allyl acetate in the presence of a catalyst selected from the group consisting of a phosphine complex of a metal selected from the group consisting of palladium, ruthenium and rhodium and a phosphine composition containing a metal selected from the group consisting of palladium, ruthenium and rhodium.

12. The method of claim 1, wherein the acetoxysiloxanes are prepared by reacting an organo(poly)siloxane having hydrogen bonded directly to silicon with an allyl acetate in the presence of a catalyst selected from the group consisting of a phosphine complex of a metal selected from the group consisting of palladium, ruthenium and rhodium and a phosphine composition containing a metal selected from the group consisting of palladium, ruthenium and rhodium.

13. The method of claim 1, wherein the catalyst is present in an amount of from 50 to 1000 parts per million based on the elemental metal and the combined weight of the organo(poly)siloxane and the allylhalide or allyl acetate.

14. The method of claim 1, wherein the allylhalide or allyl acetate is present in an amount of from 0.5 to 5 mols per gram per atom of hydrogen bonded directly to silicon.

* * * * *